(12) United States Patent
Saito

(10) Patent No.: US 7,002,032 B2
(45) Date of Patent: Feb. 21, 2006

(54) ORGANIC COMPOUND FOR CVD RAW MATERIAL AND METHOD OF MANUFACTURING METALLIC OR METALLIC COMPOUND THIN FILM USING THE ORGANIC COMPOUND

(75) Inventor: Masayuki Saito, Hiratsuka (JP)

(73) Assignee: Tanaka Kikinzoku Kogyo K.K., Tokyo (JP)

(*) Notice: Subject to any disclaimer, the term of this patent is extended or adjusted under 35 U.S.C. 154(b) by 8 days.

(21) Appl. No.: 10/491,825

(22) PCT Filed: Aug. 4, 2003

(86) PCT No.: PCT/JP03/09861

§ 371 (c)(1),
(2), (4) Date: Apr. 6, 2004

(87) PCT Pub. No.: WO2004/024980

PCT Pub. Date: Mar. 25, 2004

(65) Prior Publication Data

US 2004/0247911 A1    Dec. 9, 2004

(30) Foreign Application Priority Data

Aug. 7, 2002    (JP) .............................. 2002-230271

(51) Int. Cl.
*C07F 15/00* (2006.01)
*C07F 17/00* (2006.01)
*C23C 16/00* (2006.01)

(52) U.S. Cl. ..................... 556/136; 106/1.21; 106/128; 427/248.1; 427/587

(58) Field of Classification Search ................ 556/136; 106/1.21, 128; 427/248.1, 587
See application file for complete search history.

(56) References Cited

U.S. PATENT DOCUMENTS 5,952,047 A * 9/1999 Tasaki et al. ................ 427/252
6,037,485 A * 3/2000 Tasaki et al. .................. 556/1

FOREIGN PATENT DOCUMENTS

| JP | 10-324970 | 12/1998 |
| WO | WO 98/00432 | 1/1998 |

* cited by examiner

Primary Examiner—Porfirio Nazario-Gonzalez
(74) Attorney, Agent, or Firm—Rothwell, Figg, Ernst & Manbeck, P.C.

(57) ABSTRACT

The present invention provides an organic compound for CVD raw material prepared by mixing a first organometallic compound and at least one second organometallic compound, said first organometallic compound having a central metal atom and at least one ligand coordinated thereto and said second organic compound having the same central metal as that of the first organometallic compound and at least one different ligand coordinated thereto from the ligand of the first organometallic compound, wherein the first and second organometallic compounds differ in decomposition behavior. In particular, a CVD raw material having both easy handling and good adhesiveness to thin film, which have not been so far sufficiently compatible with each other, can be obtained by mixing a cyclopentadienyl complex or a derivative thereof as the first organometallic compound, and a β-diketonato compound as the second organometallic compound.

7 Claims, No Drawings

ORGANIC COMPOUND FOR CVD RAW MATERIAL AND METHOD OF MANUFACTURING METALLIC OR METALLIC COMPOUND THIN FILM USING THE ORGANIC COMPOUND

CROSS REFERENCE TO RELATED APPLICATION

This application is a 35 USC § 371 National Phase Entry Application from PCT/JP03/09861, filed Aug. 4, 2003, and designating the U.S., which claims priority of JP 2002-230271 filed Aug. 7, 2002.

TECHNICAL FIELD

The present invention relates to a raw material for forming a metallic thin film or a metallic compound thin film by a chemical vapor deposition method.

BACKGROUND ART

A chemical vapor deposition method (hereinafter, referred to as "CVD" method) is a film-formation process widely used in forming various metallic or metallic compound thin films. This is because a uniform thin film can be easily manufactured by the CVD method and the step coverage obtained by the CVD method is better than by a sputtering method. Particularly in recent years, a precious metal such as ruthenium or iridium has come to be used in manufacturing a thin film electrode material of a semiconductor device such as DRAM and FERAM. The CVD method is suitably used in a manufacturing process for such a precious metallic thin film.

In the CVD method, a raw-material chemical compound is gasified and transferred onto a substrate, and then decomposed and oxidized on the substrate, thereby precipitating or depositing a desired thin film constituting substance to obtain a thin film. Therefore, the raw material chemical compound for CVD preferably has a low melting point in order to vaporize easily, and causes a reaction rapidly on the substrate. As a compound having these characteristics, an organometallic compound is mentioned and generally used in a CVD method. The organometallic compound used herein is a complex compound having a target metal element for manufacturing a thin film used as the central metal, with which various substituents are coordinated.

As a raw material for forming a precious metallic thin film by CVD, various organic precious metallic compounds are known. Taking ruthenium as an example, a bis(ethylcyclopentadienyl)ruthenium represented by the following formula has been studied as an organic ruthenium compound to be put to practical use. This organic ruthenium compound is one of derivatives of ruthenocen(bis(cyclopentadienyl)ruthenium), which is a cyclopentadienyl complex having ruthenium as a central metal and two cyclopentadienyl groups coordinated therewith.

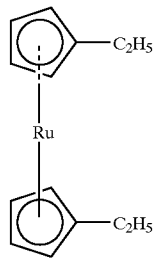

Formula 1

The bis(ethylcyclopentadienyl)ruthenium has a low melting point and is liquid at room temperature, so that it is easy to handle. In addition, it has a high vapor pressure, so that the manufacturing efficiency of a thin film is high. Therefore, this is considered suitable for CVD raw material.

Furthermore, in view of reducing the manufacturing cost for a thin film and making effective use of resources, introduction of recycling technology for CVD raw material has been considered. To recycle the CVD raw material, it is necessary to separate and purify an unreacted compound efficiently from a used material. Since bis(ethylcyclopentadienyl)ruthenium has a high vapor pressure and a good thermal stability, an unreacted bis(ethylcyclopentadienyl) ruthenium is relatively easily separated and purified, and thus efficiently reutilized by using appropriate means such as distillation.

On the other hand, another organic ruthenium compound for CVD raw material, tris(β-diketonato)ruthenium represented by the following formula is also known. The organic ruthenium compound has ruthenium as a central metal and three β-diketones coordinated therewith.

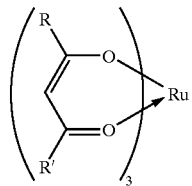

Formula 2

Tris(β-diketonato)ruthenium is characterized in that it can form a thin film having high adhesiveness to $SiO_2$. It means that it can provide a thin film excellent in adhesiveness to a semiconductor substrate, which is often formed of $SiO_2$ or a $SiO_2$ film.

DISCLOSURE OF THE INVENTION

As an example of a raw material for such a ruthenium thin film manufacturing material, bis(ethylcyclopentadienyl)ruthenium has an advantage in that it can be efficiently used to manufacture a high-purity coating film excellent in homology and can be recycled; however, it has a disadvantage in that the adhesiveness to $SiO_2$ is relatively low. In contrast, a tris(β-diketonato)ruthenium compound has good adhesiveness to a substrate. The state of a tris(β-diketonato)ruthenium compound at varies depending upon the substituent, however, most of them are solid room temperature. Therefore, it is difficult to handle it. In addition, most of them have a low vapor pressure. Therefore, the film-formation conditions for manufacturing a thin film with good quality must be strictly controlled. Since the vapor pressure of the compound is low, it is difficult to separate an unreacted compound from a used material to purify it, in other words, the recycle use of this compound is difficult. In short, there are possible organic ruthenium compounds to be used for CVD; however, none of them satisfy all requisite characteristics.

Such a problem is not limited to raw materials for manufacturing ruthenium thin films but commonly seen in many CVD raw materials for manufacturing metallic thin films. For example, a CVD raw material is required to satisfy various properties including thin film growing rate, purity of thin film, morphology besides handling and adhesiveness. However, raw materials for various metallic thin films hitherto known each have drawbacks and advantages, so that there are no materials satisfying all requirements at present.

The present invention was carried out against the background mentioned above and it is an object of the present invention to provide a method of preparing a raw material having requisite properties for manufacturing a metallic thin film or metallic compound thin film by a CVD method and provide the raw material prepared by the method.

To attain the object, the present inventors started investigation from the analysis of a thin film formation process by a CVD method. From the analysis, they presumed the composition of a preferable compound. The CVD thin film formation process is roughly classified into two steps. The first step is called a latent period or incubation time, during which crystal nuclei generate on a substrate. In this step, numerical metal crystal nuclei are scattered on the substrate while growing horizontally along the substrate but do not form a film (hereinafter, the first step will be referred to as a "first stage" or a "latent period").

Actually, a thin film starts growing in the second step in which a thin film formation reaction of a raw-material gas is facilitated by the help of a catalytic function of the crystal nuclei generated in the first stage. As a result, rapid growth of the thin film takes place. Hereinafter, the second step will be also referred to as a "thin film growth stage".

The thin film formation process by the CVD method is constituted of a plurality of stages as mentioned above. Even if organometallic compounds are capable of manufacturing the same metallic thin film, in other words, even if organometallic compounds have the same central metal, their decomposition behaviors may differ from each other. The reason why individual compounds have different advantages is considered that the advantages of the compounds are exhibited in different stages. To explain more specifically, the adhesiveness of the thin film to be manufactured to a substrate seems to be determined by the behavior of the first stage, for example, the number of generated crystal nuclei and the rate of horizontal growth of the crystal nuclei. The organometallic compound capable of manufacturing a thin film having good adhesiveness has a specific behavior in this stage. On the other hand, the morphology and purity of the thin film are determined depending upon the behavior of the thin film in its growth stage, for example, the thin film formation rate of a raw-material compound.

Based on the analysis mentioned above, the present inventors conceived that a CVD raw material having advantages may be obtained if the behaviors in each of the stages can be improved. They reached a specific idea that a plurality of organometallic compounds each having desired characteristic are mixed to prepare a CVD raw material.

More specifically, the present invention provides an organic compound used in CVD as a raw material, which is formed by mixing a first organometallic compound having a metal atom and a ligand coordinated therewith, and at least one second organic compound having the same metal atom of the first organometallic compound and a different ligand coordinated therewith and different in behavior from the first organometallic compound.

The metal to be used in manufacturing a thin film according to the present invention is not particularly limited. The object of the present invention can be attained by using a desired metal as a central metal of each of the organometallic compound serving as a main component and the organometallic compound serving as an accessory component. The present invention is useful for manufacturing a thin film of a precious metal such as ruthenium, iridium, platinum, gold, silver, rhodium, palladium, or osmium. By using an organometallic compound having a central metal selected from these, the precious metallic thin film can be efficiently manufactured.

A CVD raw material according to the present invention may be formed by manufacturing a first organometallic compound and a second organometallic compound and mixing both compounds. Each of the organometallic compound may be manufactured by a know method.

A CVD raw material obtained by the method of the present invention not only provides a thin film having good adhesiveness but also has easiness in handling as a raw material. The present inventors figured out possible combinations of organometallic compounds which might satisfy both thin-film adhesiveness and easiness in handling based on the following discussion and investigated on specific combinations.

To improve the thin-film adhesiveness, it is preferable to use an organometallic compound having a good decomposition behavior in the first stage of the thin film formation process. On the assumption that a thin film is formed on a general substrate formed of an oxide such as $SiO_2$, the present inventors thought that a preferable organic compound has intra-molecular oxygen, which forms a metal-oxygen bond (M—O bond). This is because, if the M—O bond is present in a molecule, the crystal nuclei having a composition very closer to that of an oxygen-rich metal oxide may precipitate in the first stage. Since the crystal nuclei having an analogous composition to an oxide is considered to have high adhesiveness to a substrate formed of the oxide, the adhesiveness to the thin film may be improved. Based on this, the present inventors conceived that an organometallic compound (represented by the following formula) having β-diketone ligands coordinated to a metal is preferred as a compound for CVD raw material having an M—O bond.

Formula 3

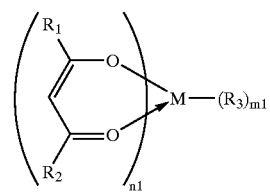

where $R_1$ and $R_2$ constituting a β-diketonato compound independently represent hydrogen or any one selected from the group consisting of alkyl and alkoxyl groups; $R_3$ represents any one selected from the group consisting of alkyls, alkenes, cyclopentadienes, cyclooctadienes, norbornadienes, and carbonyl, or the same β-diketone having $R_1$ and $R_2$ defined above; M represents a central metal element; $n_1$ is an integer of 1 to 3; and $m_1$ is an integer of 0 to 2.

On the other hand, to ensure good handling of a CVD raw material, the present inventors thought it desirable to employ an organometallic compound having a high vapor pressure and being liquid at room temperature, since this organometallic compound determines the entire handling of the CVD raw material and the growth rate of the thin film. More specifically, it is desirable that an organometallic compound have a vapor pressure of 0.1 torr or more at 100° C. and be liquid at 60° C. or less.

Specific organometallic compounds having such properties have been investigated. As a result, a cyclopentadienyl complex having at least one cyclopentadienyl ligand, represented by the following formula, and derivatives thereof have been found to be preferable.

Formula 4

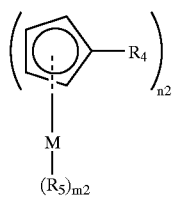

where $R_4$ represents hydrogen or any one selected from the group consisting of alkyl, alkene, alkoxyl and acetyl groups; $R_5$ represents any one selected from the group consisting of alkyl, alkene, alkoxyl and acetyl groups; M represents a central metal element; and $n_2$ is an integer of 1 to 2 and $m_2$ is an integer of 0 to 2.

The cyclopentadienyl complex has a high vapor pressure and a low melting point, so that it is usually liquid at normal temperature. Therefore, the cyclopentadienyl complex is preferable as a main component of a CVD raw material. A cyclopentadienyl complex, even if it is solid at normal temperature, can be converted to a liquid state by converting it to a derivative thereof and thereby lowering a melting point. The derivative of a cyclopentadienyl complex used herein means a compound having a cyclopentadienyl group wherein at least one hydrogen is replaced by a different substituent. As the substituent, an alkyl group such as methyl, ethyl or propyl is preferable.

Furthermore, since a cyclopentadienyl complex and a derivative thereof have high vapor pressures, an unreacted cyclopentadienyl complex and a derivative thereof can be taken out from a used material after a thin film is formed and subjected to recycle use.

According to the present inventors, when a cyclopentadienyl complex and a β-diketonato compound are mixed and used as a CVD raw material, the thin film is grown at virtually the same rate as the case where a cyclopentadienyl complex alone is used; however, it was confirmed that the latent period is reduced. This is conceivable that the β-diketonato compound added in the CVD raw material influences the nuclei generation during the latent period, generating crystalline nuclei in high density.

It is preferable that the content of a β-ketonato compound (an organic compound responsible for thin film formation in the first stage and imparting adhesiveness) be smaller than that of a cyclopentadienyl complex (an organometallic compound contributing to film growth stage). What is important in the first stage of the thin film formation is the rate of forming crystalline nuclei. The amount of crystalline nuclei is not critical. As described above, the crystalline nuclei formed in the first stage are not a film-like nuclei but as a substance serving as a catalyst for accelerating the later thin film growth. Therefore, it is satisfactory if the crystalline nuclei present a little. For this reason, a compound such as a β-diketonato compound responsible for forming crystalline nuclei may be contained a little. Even if the content of a β-diketonato compound is more than needed, the β-diketonato compound have no effect upon the thin film growth stage; conversely, the content of a cyclopentadienyl complex is reduced, with the result that the thin film growth may be negatively affected. In addition, it is difficult to recycle β-diketonato compound in most cases. If the content of a β-diketonato compound increases, the recycling rate decreases, raising device cost.

In these circumstances, the content of a β-diketonato compound is preferably set from 0.2 to 20% by weight. This is because if the content is less than 0.2% be weight, it has no effect upon the thin film growth in the first stage and if the content exceeds 20% by weight, it may inhibit the thin film growth.

In particular, in manufacturing a ruthenium thin film, the raw material may be prepared by mixing bis(ethylcyclopentadienyl)ruthenium in place of a cyclopentadienyl complex, and tris(β-diketonato)ruthenium in place of a β-diketonato compound. The raw material thus prepared is preferable because it has both characteristics: one is good-handling and recyclability given by bis(ethylcyclopentadienyl)ruthenium and the other is adhesiveness to a thin film given by tris(β-diketonato)ruthenium. As is shown in the example of a mixed material of a cyclopentadienyl complex and a β-ketonato compound, according to a CVD raw material of the present invention, desired characteristics required for CVD raw material can be obtained. The thin film manufacturing method using a CVD raw material according to the present invention makes it possible to efficiently manufacture a thin film with good quality.

BEST MODE FOR CARRYING OUT THE INVENTION

Preferable example of the present invention will be described below.

In this example, tris(2,4-pentanedionato)ruthenium as an accessory component and bis(ethylcyclopentadienyl)ruthenium as a main component were prepared. Both compounds were mixed to prepare a CVD raw material. Using the CVD raw material, a ruthenium thin film was manufactured.

Preparation of tris(2,4-pentanedionato)ruthenium

A ruthenium trichloride hydrate was placed in a separable flask of 5 L in volume so as to contain 80.15 g of ruthenium. To the flask, further 3,500 mL of water and 297.5 g of 2,4-pentanedione were added and refluxed in the air for 2 hours. To the resultant solution, 330 g of sodium acid carbonate was added and refluxed for another 2 hours. From the obtained reaction solution, the organic phase was extracted, vaporized, and dried to obtain 285.3 g of tris(2,4-pentanedionato)ruthenium as a red crystal.

Preparation of bis(ethylcyclopentadienyl)ruthenium

To a nitrogen-replaced flask, 5.0 mL of a hexane solution containing n-butyllithium (concentration: 2.6 mol/L) was placed and cooled to −78° C. After 1.74 g of bis(cyclopentadienyl)ruthenium was added, 50 mL of tetrahydrofuran was added dropwise over one hour to react them. The reaction solution was allowed to stand for 2 hours to return the temperature to room temperature and thereafter a reaction was performed for 24 hours. The reaction solution was again cooled to −78° C., 9.81 g of ethyl bromide was added dropwise over one hour to react them, allowed to stand for 2 hours to room temperature, and the reaction was performed for 24 hours. After completion of the reaction, 100 mL of water was added and bis(ethylcyclopentadienyl) ruthenium was extracted with hexane and then hexane was evaporated from the extraction solvent to obtain 2.0 g of bis(ethylcyclopentadienyl) ruthenium.

Preparation of CVD Raw Material

The tris(2,4-pentanedionato)ruthenium and bis(ethylcyclopentadienyl)ruthenium were mixed to produce a CVD raw material. To this mixture, tris(2,4-pentanedionato)ruthenium was added in an amount of 20% by weight. The mixture was liquid at room temperature.

Manufacture of Ruthenium Thin Film

A ruthenium thin film was manufactured by a CVD method using the CVD raw material obtained above. The thin film was manufactured by vaporizing a solution of the CVD raw material by an evaporator and supplying it as a raw material gas onto a substrate. The thin film manufacturing conditions are as follows:

Material supply rate: 0.05 g/min
Vaporization temperature: 190° C.
Carrier gas: argon (200 sccm)
Reaction gas: oxygen (200 sccm)
Chamber pressure: 665 Pa (5 torr)
Substrate: SiO$_2$ wafer
Substrate temperature: 250° C.
Film formation time: 20 minutes In the film formation process, a ruthenium thin film was successfully manufactured without any problem. The thickness of the ruthenium thin film thus obtained was 120 nm.

Comparative Example

As a Comparative Example, only the bis(ethylcyclopentadienyl)ruthenium obtained above was used as a CVD raw material to manufacture a ruthenium thin film. The same film formation conditions as above were employed. In manufacturing the thin film, a ruthenium thin film was also manufactured without any problem. The thickness of the ruthenium thin film thus obtained was 90 nm.

An experiment was performed to investigate the adhesiveness of the manufactured thin film to a substrate (hereinafter the experiment will be referred to as a "peel test"). The peel test was performed as follows. After a thin film was formed on a wafer, a 5 mm×5 mm grid was formed in the range of a 2 cm×2 cm square on the wafer to obtain 16 grids in total and commercially available adhesive cellophane tape was adhered and then peeled away. The number of removed ruthenium thin-film grids was counted. The peel test was performed with respect to 10 substrates.

As the result of the peel test, the number of removed thin film grids (the total number of grids peeled away in 10 peel tests) was zero in Example; however 35 in Comparative Example. Therefore, it was demonstrated that the thin film manufactured from the CVD raw material produced in Example has good adhesiveness to a substrate.

INDUSTRIAL APPLICABILITY

As explained in the foregoing, the compound for CVD raw material according to the present invention may have preferably characteristics. In particular, according to the present invention, it is possible to obtain a thin film easy-to-handle and having high adhesiveness to a substrate.

Therefore, a thin film of ruthenium or a ruthenium compound having good properties can be manufactured with a high manufacturing efficiency. The thin film can be recycled, contributing to reduction of thin-film manufacturing cost, leading to reduction of device manufacturing cost.

The invention claimed is:

1. An organic compound for CVD raw material prepared by mixing a first organometallic compound and at least one second organometallic compound, said first organometallic compound having a central metal atom and at least one ligand coordinated thereto and said second organometallic compound having the same central metal as that of the first organometallic compound and coordinated thereto at least one ligand different from the ligand of the first organometallic compound, said first and second organometallic compounds differ in decomposition behavior, wherein the first organometallic compound is a cyclopentadienyl complex or a derivative thereof represented by the following formula:

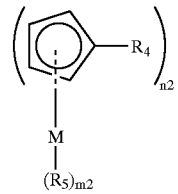

Formula 4 where R$_4$ represents hydrogen or a member selected from the group consisting of alkyl, alkene, alkoxyl and acetyl groups; R$_5$ represents a member selected from the group consisting of alkyl, alkene, alkoxyl and acetyl groups; M represents a central metal element; n$_2$ is an integer of 1 to 2; and m$_2$ is an integer of 0 to 2.

2. The organic compound for CVD raw material according to claim 1, wherein the second organometallic compound is a β-diketonato compound represented by the following formula:

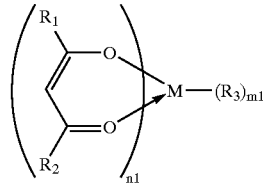

Formula 3 where R$_1$ and R$_2$ independently represent hydrogen or a member selected from the group consisting of alkyl and alkoxyl groups; R$_3$ represents a member selected from the group consisting of alkyl, alkene, cyclopentadiene, cyclooctadiene, norbornadiene and carbonyl, or the same β-diketone having R$_1$ and R$_2$ defined above; M represents a central metal element; n$_1$ is an integer of 1 to 3: and m$_1$ is an integer of 0 to 2.

3. The organic compound for CVD raw material according to claim 1, wherein the central metal is selected from the group consisting of ruthenium, iridium, platinum, gold, silver, rhodium, palladium, and osmium.

4. A method of manufacturing a metallic or metallic compound thin film comprising vaporizing the organic compound for CVD raw material according to claim 1 and transporting the vaporized organic compound onto a substrate.

5. The organic compound for CVD raw material according to claim 1, wherein the first organometallic compound is a bis(ethylcyclopentadienyl) and the second organometallic compound is a tris(β-diketonato) ruthenium.

6. The organic compound for CVD raw material according to claim 1, wherein the content of the second organometallic compound is from 0.2 to 20% by weight based on the weight of said organic compound.

7. The organic compound for CVD raw material according to claim 1, wherein $n_2=2$ and $m_2=0$ in the first organometallic compound, which is represented by the following formula:

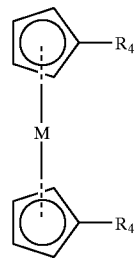

* * * * *